(12) United States Patent
Redei et al.

(10) Patent No.: US 9,951,387 B2
(45) Date of Patent: Apr. 24, 2018

(54) METHODS FOR DETECTION OF DEPRESSIVE DISORDERS

(71) Applicant: Northwestern University, Evanston, IL (US)

(72) Inventors: Eva Redei, Chicago, IL (US); Brian Andrus, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/296,807

(22) Filed: Oct. 18, 2016

(65) Prior Publication Data

US 2017/0037473 A1    Feb. 9, 2017

Related U.S. Application Data

(60) Continuation of application No. 14/994,802, filed on Jan. 13, 2016, now Pat. No. 9,469,875, which is a division of application No. 13/276,565, filed on Oct. 19, 2011, now abandoned.

(60) Provisional application No. 61/394,449, filed on Oct. 19, 2010.

(51) Int. Cl.
*C12Q 1/68* (2018.01)
*G01N 33/68* (2006.01)

(52) U.S. Cl.
CPC ....... *C12Q 1/6883* (2013.01); *G01N 33/6893* (2013.01); *C12Q 2600/156* (2013.01); *C12Q 2600/158* (2013.01); *G01N 2800/304* (2013.01); *G01N 2800/60* (2013.01)

(58) Field of Classification Search
None
See application file for complete search history.

*Primary Examiner* — Addison D Ault
(74) *Attorney, Agent, or Firm* — Casimir Jones SC; David Staple

(57) ABSTRACT

The present invention relates generally to the detection or diagnosis of depressive disorders, and provides methods and compositions useful for this purpose. In particular, the present invention provides biomarkers for the detection or diagnosis of major depressive disorder, and methods of use thereof.

2 Claims, 2 Drawing Sheets

METHODS FOR DETECTION OF DEPRESSIVE DISORDERS

CROSS REFERENCE TO RELATED APPLICATIONS

The present application is a continuation of U.S. patent application Ser. No. 14/994,802, filed Jan. 13, 2016, which is a divisional of abandoned U.S. patent application Ser. No. 13/276,565, filed Oct. 19, 2011, which claims the benefit of U.S. Provisional Patent Application Ser. No. 61/394,449, filed Oct. 19, 2010, each of which is incorporated by reference in its entirety.

FIELD OF THE INVENTION

The present invention relates generally to the detection or diagnosis of depressive disorders, and provides methods and compositions useful for this purpose. In particular, the present invention provides biomarkers for the detection or diagnosis of major depressive disorder, and methods of use thereof.

BACKGROUND OF THE INVENTION

Depressive disorders (e.g. Major depressive disorder (MDD)) are the leading cause of disability in the United States when measured as total time lost to disability, affecting more than 18 million people annually in the USA alone. Depressive disorders, the most common of affective illnesses, include a large set of illnesses ranging from seasonal depressive disorder to chronic depression. There are currently no known available biological markers for depression; diagnosis is made by physicians or psychologists based on structured interviews with the patients. Depressive disorders are among only a few major illnesses that remain reliant upon subjective diagnoses. This contributes to under recognition, trivialization and stigmatization of these disabling illnesses.

Pre-adult onset of MDD, which occurs most often during adolescence, occurs in approximately 40% of patients with MDD. This sub-group has a poor prognosis, with high levels of adult affective disorder, substance use disorders, physical illness, and social maladjustment. This dysfunction includes problematic parenting behaviors in both women and men, with negative consequences for offspring. Thus, the public health benefit of treating adolescent MDD affects not only teens, but subsequent generations as well. In addition, the disorder is the major psychiatric risk factor for teen suicide, with rates in this group being more than 20 times greater than in the general adolescent population.

Treatments for adolescent MDD exist but response rates vary, medication side effects are unpredictable, and adolescents have lower response rates than adults. Exacerbating the problem is that 40% of youths with clinically significant levels of depression never come to the attention of a medical or mental health care provider. Many of these issues with treatment and identification are due, at least in part, to a diagnostic process that relies primarily on patient self-report. While symptom report is critical to the diagnostic process, it is subject to recall bias, the vagaries of culture-, gender-, education-influenced interpretations by the patients, and in the case of parent-report, the parent's own psychological state. Symptoms and signs, therefore, do not always discriminate between youths with and without MDD. The current diagnostic practice results in some youths who need treatment but are not getting it, and some who get treatment but may not need it. MDD treatments (e.g. anti-depressants and psychotherapy) carry risks of adverse effects, and the economic cost of inappropriate treatment is high, as the effects of antidepressant medication on the developing adolescent brain are not completely understood. Conversely, the individual, societal, and economic costs of not treating a youth who truly does have MDD can also be quite high, and include suicide, hospitalization, and/or protracted impairment. The costs of misclassification for research studies are also significant in wasted dollars, time, and incorrect results.

SUMMARY OF THE INVENTION

In some embodiments, the present invention provides a method for assessing depressive disorders in a subject, comprising: (a) providing a sample from a subject; (b) characterizing the levels of gene expression of one or more genes selected from the genes listed in Tables 1 and 4; and (c) identifying risk of depressive disorders in the subject based on the levels of gene expression and/or protein expression. In some embodiments, the subject is a human subject. In some embodiments, the human subject is suspected of suffering from depressive disorder.

In some embodiments, the subject is suspected of suffering from MDD. In some embodiments, assessing depressive disorders comprises: detecting, quantifying, diagnosing, indicating, or determining the presence, risk, severity, and/or type of depressive disorder.

In some embodiments, the subject is an adolescent. In some embodiments, the genes comprise one or more of the genes listed in Table 1. In some embodiments, the genes comprise a variant of one or more of the genes listed in Table 1 (e.g. >50% identity, >60% identity, >70% identity, >80% identity, >90% identity, >95% identity, >98% identity, >99% identity). In some embodiments, the genes comprise one or more of the genes listed in Table 4. In some embodiments, the genes comprise a variant of one or more of the genes listed in Table 4 (e.g. >50% identity, >60% identity, >70% identity, >80% identity, >90% identity, >95% identity, >98% identity, >99% identity). In some embodiments, the genes comprise one or more of ADCY3, ATP2C1, CD59, FAM46A, FMR1, GNAQ, IGSF4A/CADM1, MAF, MARCKS, NAGA, PTPRM, TLR7, and ZNF291/SCAPER.

In some embodiments, the subject is an adult. In some embodiments, the genes comprise one or more of the genes listed in Table 1. In some embodiments, the genes comprise one or more of FAM46A, MARCKS, ATP2C1, NAGA, TLR7, ADCY3, ASAH1, CD59, FOS, IGSF4A/CADM1, ZNF291/SCAPER, ATP11C, MAF, GNAQ, FMR1, and PTPRM. In some embodiments, the genes comprise one or more of FAM46A, CD59, IGSF4A/CADM1, NAGA and TLR7.

In some embodiments, characterizing the levels of gene expression comprises detecting the amount of mRNA. In some embodiments, detecting the amount of mRNA comprises exposing a sample to nucleic acid probes complementary to the mRNA. In some embodiments, nucleic acid probes are covalently linked to a solid surface. In some embodiments, detecting the amount of mRNA in a sample comprises use of a detection technique selected from the group consisting of microarray analysis, reverse transcriptase PCR, quantitative reverse transcriptase PCR, and hybridization analysis.

In some embodiments, characterizing the levels of gene expression comprises detecting the amount of protein (e.g.

in a sample). In some embodiments, detecting the amount of protein comprises using antibodies, antibody fragments, or other protein binding agents.

In some embodiments, the present invention provides kits and/or panels for detecting depressive disorders in subjects, comprising reagents for detecting two or more genes listed in Tables 1 and/or 4, or proteins encoded thereby. In some embodiments, the subject is a human subject. In some embodiments, the genes comprise a variant of one or more of the genes listed in Table 1 (e.g. >50% identity, >60% identity, >70% identity, >80% identity, >90% identity, >95% identity, >98% identity, >99% identity). In some embodiments, the genes comprise one or more of the genes listed in Table 4. In some embodiments, the genes comprise a variant of one or more of the genes listed in Table 4 (e.g. >50% identity, >60% identity, >70% identity, >80% identity, >90% identity, >95% identity, >98% identity, >99% identity). In some embodiments, the genes comprise one or more of ADCY3, ATP2C1, CD59, FAM46A, FMR1, GNAQ, IGSF4A/CADM1, MAF, MARCKS, NAGA, PTPRM, TLR7, and ZNF291/SCAPER. In some embodiments, the subject is an adult. In some embodiments, the genes comprise one or more of the genes listed in Table 1. In some embodiments, the genes comprise one or more of FAM46A, MARCKS, ATP2C1, NAGA, TLR7, ADCY3, ASAH1, CD59, FOS, IGSF4A/CADM1, ZNF291/SCAPER, ATP11C, MAF, GNAQ, FMR1, and PTPRM. In some embodiments, the genes comprise one or more of FAM46A, CD59, IGSF4A/CADM1, NAGA and TLR7.

In some embodiments, the present invention provides methods for assessing chronic stress in a subject, comprising: (a) characterizing the levels of gene expression of one or more genes in a sample from a subject, wherein said one or more genes are selected from the genes listed in Table 2; and (b) identifying risk of chronic stress in said subject based on said levels of gene expression. In some embodiments, the subject is a human subject. In some embodiments, the genes comprise a variant of one or more of the genes listed in Table 2 (e.g. >50% identity, >60% identity, >70% identity, >80% identity, >90% identity, >95% identity, >98% identity, >99% identity).

In some embodiments, the present invention provides kits or panels for detecting chronic stress in a subject comprising reagents for detecting two or more genes listed in Table 2, or proteins encoded thereby. In some embodiments, the subject is a human subject. In some embodiments, the subject is a human subject. In some embodiments, the genes comprise a variant of one or more of the genes listed in Table 2 (e.g. >50% identity, >60% identity, >70% identity, >80% identity, >90% identity, >95% identity, >98% identity, >99% identity).

DETAILED DESCRIPTION OF THE INVENTION

Figure 1:
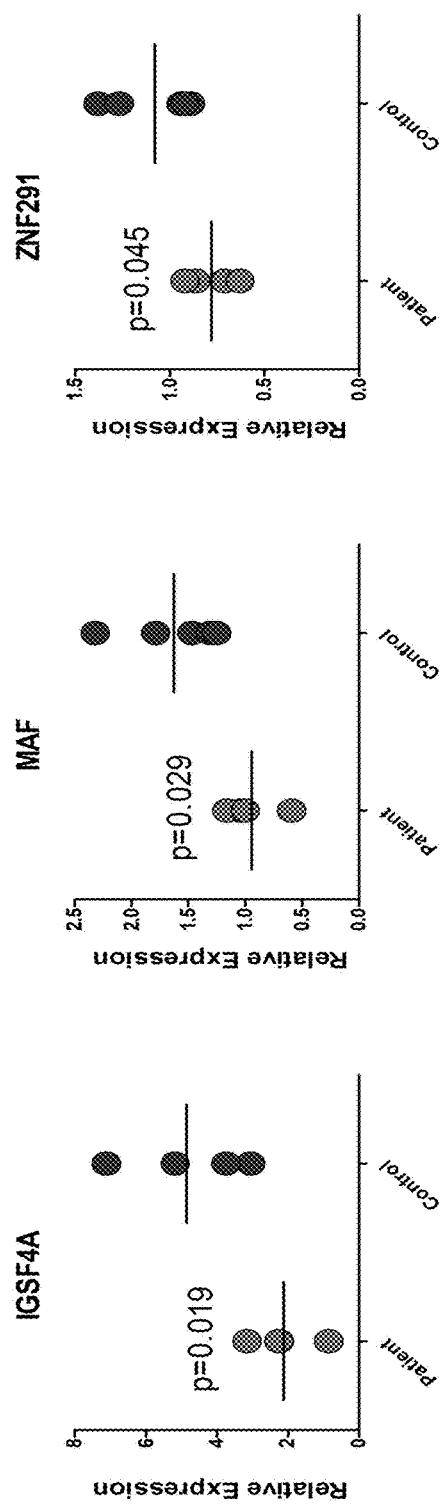
FIG. 1 shows plots validating adolescent biomarker genes by quantitative RT-PCR; RNA was prepared from the blood of adolescents with MDD and ND controls; the amounts of specific mRNA were normalized to 18s rRNA expression.

Depressive disorders (e.g. MDD) are the leading cause of disability in the United States when measured as total time lost to disability, affecting more than 18 million people annually in the USA alone. Depressive disorders, the most common of affective illnesses, include a large set of illnesses from seasonal depressive disorder to chronic depression. There are currently no known biological markers for depression; diagnosis is made by physicians or psychologists based on structured interviews with the patients. Biomarkers can improve definitive diagnosis, treatment, and potentially prevention of depression.

In some embodiments, the present invention provides biological markers indicative of and/or diagnostic of a depressive disorder. In some embodiments, biological markers are indicative of and/or diagnostic of MDD. In some embodiments, biological markers are blood biomarkers. In some embodiments, the present invention provides one or more biomarkers, or a panel of biological markers, that can be identified from tissue or blood or other sample types. In some embodiments, these biological markers show increased or decreased levels of gene-specific RNA in subjects with current depressive symptoms (e.g. MDD symptoms) compared to those of controls. In some embodiments, these biological markers show increased or decreased levels of protein expressed from these genes in subjects with current depressive symptoms (e.g. MDD symptoms) compared to those of controls. In some embodiments, the present invention assesses one or more genes from the genes listed in Tables 1 and 4. In some embodiments the present invention provides a panel of reagents for detecting genes or encoded proteins comprising one or more gene from Tables 1 and 4. In some embodiments the present invention provides a panel of reagents for detecting genes or encoded proteins consisting of one or more gene from Tables 1 and 4. In some embodiments, a panel comprises one or more reagents for detecting genes or encoded proteins from Tables 1 and/or 4 and one or more additional genes. In some embodiments, the present invention provides a set of genes whose mRNA levels differ in the blood of subjects showing higher and lower level of depressive behavior (e.g. MDD). In some embodiments, the present invention provides a set of genes whose protein levels differ in the blood of subjects showing higher and lower level of depressive behavior (e.g. MDD). In some embodiments, the present invention provides biological markers that are common between those expressed in the blood and those expressed in the brain regions of animals, showing higher and lower level of depressive behavior. In some embodiments of the present invention, one or more such genes are used to diagnose or suggest a risk of depression from human sample (e.g., blood sample). In some embodiments, the presence of a gene or panel of genes that correlates with depression (e.g. is indicative of depression, is diagnostic of depression) allows a treating physician to take any number of courses of action, including, but not limited to, further diagnostic assessment, selection of appropriate treatment (e.g., pharmaceutical, nutritional, counseling, and the like), increased or decreased monitoring, etc. In some embodiments, changes in expression of a gene or panel of genes that correlates with depression (e.g. is indicative of depression, is diagnostic of depression) allows a treating physician to take any number of courses of action, including, but not limited to, further diagnostic assessment, selection of appropriate treatment (e.g., pharmaceutical, nutritional, counseling, and the like), increased or decreased monitoring, etc.

In some embodiments the present invention provides a method for detecting or assessing the risk of depressive disorders (e.g. MDD or chronic stress) in a subject. In some embodiments the present invention provides a method for diagnosing depressive disorders (e.g. MDD) in a subject. In some embodiments the present invention provides a method for detecting or assessing the risk of depressive disorders in a subject, comprising the steps of: providing a sample from a subject (e.g., a blood sample), identifying the level of gene expression of one or more genes, wherein said one or more genes is selected from the genes listed in Tables 1, 2 and/or 4, and identifying the presence or absence or a risk of depressive disorders (e.g. MDD) in said subject based on said level of gene expression. In some embodiments the present invention provides methods for characterizing the level of gene expression of a panel of genes comprising detecting the amount of mRNA of a panel of genes of one or more of the genes listed in Tables 1, 2 and/or 4. In some embodiments, the panel comprises 1, 2, 3, 4, 5, 6, 7, 8, 9, 10, 11, 12, 13, 14, 15, 16, 17, 18, 19, 20 ... 30 ... 40, etc. genes. In some embodiments the present invention provides methods comprising the step of exposing a sample to nucleic acid probes complementary to said mRNA of a panel of genes from the genes listed in Tables 1, 2 and/or 4. In some embodiments the methods employ a nucleic acid detection technique comprising one or more of microarray analysis, reverse transcriptase PCR, quantitative reverse transcriptase PCR, and hybridization analysis. In some embodiments the present invention provides a method for detecting depressive disorders (e.g MDD) in a human subject.

In some embodiments the present invention provides methods for characterizing the level of gene expression of a panel of genes comprising detecting the amount of protein (e.g. in the blood) expressed by a panel of genes of one or more of the genes listed in Tables 1, 2 and/or 4. In some embodiments the present invention provides methods detecting changes in the amount of protein (e.g. in the blood) expressed by a panel of genes of one or more of the genes listed in Tables 1, 2 and/or 4. In some embodiments, the panel comprises 1, 2, 3, 4, 5, 6, 7, 8, 9, 10, 11, 12, 13, 14, 15, 16, 17, 18, 19, 20 . . . 30 . . . 40, etc. genes. In some embodiments the present invention provides methods comprising the step of exposing a sample to antibodies for the proteins expressed by a panel of genes from the genes listed in Tables 1, 2 and/or 4. In some embodiments, detecting a change in the expression of one or more of the genes listed in Tables 1 and/or 3 comprises exposing a sample to containing the one or more biomarkers to antibodies specific to the biomarkers and detecting the binding of the antibodies to the biomarkers. In some embodiments the present invention provides a method for detecting depressive disorders (e.g. MDD) in a human subject.

In some embodiments, the present invention provides biomarkers for depressive disorders (e.g. MDD) in adolescents (e.g. biomarkers of Table 4). In some embodiments, altered expression of one or more biomarkers of adolescent depression (e.g. MDD) is indicative and/or diagnostic for adolescent depression (e.g. MDD). In some embodiments, increased expression of one or more biomarkers of adolescent depression (e.g. MDD) is indicative and/or diagnostic for adolescent depression (e.g. MDD). In some embodiments, decreased expression of one or more biomarkers of adolescent depression (e.g. MDD) is indicative and/or diagnostic for adolescent depression (e.g. MDD). In some embodiments, altered (e.g. increased and/or decreased) expression of one or more biomarkers (e.g. 1, 2, 3, 4, 5, 6, 7, 8, 9, 10, 11, 12, 13) selected from of ADCY3, ATP2C1, CD59, FAM46A, FMR1, GNAQ, IGSF4A/CADM1, MAF, MARCKS, NAGA, PTPRM, TLR7, and ZNF291/SCAPER is indicative and/or diagnostic for adolescent depression (e.g. MDD). In some embodiments, altered (e.g. increased and/or decreased) expression of one or more biomarkers (e.g. 1, 2, 3, 4, 5, 6, 7, 8, 9, 10, 11, 12, 13) selected from of ADCY3, ATP2C1, CD59, FAM46A, FMR1, GNAQ, IGSF4A/CADM1, MAF, MARCKS, NAGA, PTPRM, TLR7, and ZNF291/SCAPER demonstrates an increased risk adolescent depression (e.g. MDD).

In some embodiments, the present invention provides biomarkers for depressive disorders (e.g. MDD) in adults (e.g. biomarkers of Table 1). In some embodiments, altered expression of one or more biomarkers of adult depression (e.g. MDD) is indicative of and/or diagnostic for adult depression (e.g. MDD). In some embodiments, altered expression of one or more biomarkers of adult depression (e.g. MDD) is indicative of increased risk of adult depression (e.g. MDD). In some embodiments, increased expression of one or more biomarkers of adult depression (e.g. MDD) is indicative and/or diagnostic for adult depression (e.g. MDD). In some embodiments, decreased expression of one or more biomarkers of adult depression (e.g. MDD) is indicative and/or diagnostic for adult depression (e.g. MDD). In some embodiments, altered (e.g. increased and/or decreased) expression of one or more biomarkers (e.g. 1, 2, 3, 4, 5, 6, 7, 8, 9, 10, 11, 12, 13) selected from of FAM46A, MARCKS, ATP2C1, NAGA, TLR7, ADCY3, ASAH1, CD59, FOS, IGSF4A/CADM1, ZNF291/SCAPER, ATP11C, MAF, GNAQ, FMR1, and PTPRM is indicative and/or diagnostic for adult depression (e.g. MDD). In some embodiments, altered (e.g. increased and/or decreased) expression of one or more biomarkers (e.g. 1, 2, 3, 4, 5, 6, 7, 8, 9, 10, 11, 12, 13) selected from of FAM46A, MARCKS, ATP2C1, NAGA, TLR7, ADCY3, ASAH1, CD59, FOS, IGSF4A/CADM1, ZNF291/SCAPER, ATP11C, MAF, GNAQ, FMR1, and PTPRM is indicative of an increased risk of adult depression (e.g. MDD). In some embodiments, altered expression of one or both of FAM46A and TLR7 is indicative and/or diagnostic for adult depression (e.g. MDD). In some embodiments, altered expression of one ormore of FAM46A CD59, IGSF4A/CADM1, NAGA and TLR7 is indicative of an increased risk of adult depression (e.g. MDD).

In some embodiments the present invention relates to novel gene expression profiles that correlate with depressive disorders (e.g. MDD or chronic stress), and uses thereof. In some embodiments the present invention relates to novel gene expression profiles that are indicative of depressive disorders (e.g. MDD). In some embodiments the present invention relates to novel gene expression profiles that are diagnostic of depressive disorders (e.g. MDD). In some embodiments, a panel of two or more genes is analyzed (e.g. 2 genes . . . 5 genes . . . 10 genes . . . 20 genes . . . 50 genes . . . 100 genes . . . 200 genes . . . 500 genes, etc.). In some embodiments, the panel has a number of different detection reagents (e.g., oligonucleotide probes) that have specificity for genes associated with depression and identified herein (e.g. Table 1, 2 and/or 4). It is contemplated that in some embodiments samples are prepared from blood RNA samples of patients with depressive disorders and control samples, and the prepared samples are applied to the panel. It is contemplated that the differential hybridization of the patient samples relative to the control samples provides an expression signature of depressive disorders. In some embodiments, gene expression from a test sample is compared with a prior sample from the same patient to monitor changes over time. In some embodiments, gene expression from a test sample is compared with a sample from the patient under a different treatment regimen (e.g., pharmaceutical therapy) to test or monitor the effect of the therapy.

In some embodiments, gene expression from a test sample is compared to gene expression from a negative control sample (e.g., a subject known to not have depression). In some embodiments, gene expression levels from a test sample are compared to predetermined threshold levels identified (e.g., based on population averages for patients with similar age, gender, metabolism, etc.) as "normal" for individuals without depression. In some embodiments, an increase or decrease of greater than 1.2-fold (e.g., 1.5-fold, 2-fold, 3-fold, 5-fold, 10-fold, or higher) compared to "normal" levels or any increase over a normal level or threshold level is identified as at risk for depression.

A variety of known biological assays may be used to assess expression levels of depression markers. For example, in some embodiments, a microarray is used. Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is typically a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

Non-amplified or amplified nucleic acids can be detected by any conventional means. For example, in some embodiments, nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

As used herein, the term "sample" is used in its broadest sense. In one sense it can refer to biological samples obtained from animals (including humans) and encompass fluids, solids, tissues, and gases. Biological samples include blood products (e.g., plasma and serum), saliva, urine, and the like. These examples are not to be construed as limiting the sample types applicable to the present invention.

In some embodiments, a computer-based analysis program is used to translate the raw data generated by the detection assay (e.g., the presence, absence, or amount of expression a panel of genes) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a blood or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of depression being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

Compositions for use in the diagnostic methods of the present invention include, but are not limited to, probes, amplification oligonucleotides, and antibodies. Particularly preferred compositions detect the level of expression of a panel of genes. Systems and kits are provided that are useful, necessary, and/or sufficient for detecting expression of one or more genes.

Any of these compositions, alone or in combination with other compositions of the present invention, may be provided in the form of a kit. For example, the single labeled probe and pair of amplification oligonucleotides may be provided in a kit for the amplification and detection and/or quantification of a panel of genes selected from a group comprising the genes listed in Tables 1, 2 and/or 4. The kit may include any and all components necessary or sufficient for assays including, but not limited to, the reagents themselves, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered.

In some embodiments, the present invention provides therapies for diseases characterized by altered expression of disease markers identified using the methods of the present invention. In particular, the present invention provides methods and compositions for monitoring the effects of a candidate therapy and for selecting therapies for patients.

EXPERIMENTAL DATA

Example 1

Identification of MDD Biomarkers

Experiments were conducted during the development of embodiments of the invention to identify biomarkers of MDD through genome-wide expression analysis in the blood and relevant brain regions of animal models of MDD developed from a well-accepted genetic animal model of depression, the Wistar Kyoto (WKY) rat strain. Two sub-strains were developed from the WKY strain that show opposite behavior in behavioral tests used to measure depression. The WKY More Immobile (WMI) line is more depressed while the WKY Less Immobile (WLI) line is less depressed. Since these sub-strains were developed from an inbred line, their genetic variability is very small, thereby indicating that expression differences in their brain and blood are related to the behavioral differences between them.

AFFYMETRIX microarray profiling of gene expression patterns, using the Rat 230v2 AFFYMETRIX GENECHIP arrays, were carried out in the frontal cortex, amygdale, hippocampus, and striatum in both WMI and WLI males. Microarray analysis was repeated from the same brain regions using different generation animals. Microarray profiling of gene expression patterns was also carried out in the blood of WMI and WLI males. Blood microarray analysis was repeated from the $20^{TH}$ generation WMI-WLIs using ILLUMINA SENTRIX Rat (Ref-12) Expression BEAD-CHIP, version 1.0, release 1. Based on the analyses of these microarray data, a biomarker list was created using the data of blood and brain expression (Table 1).

TABLE 1

Biomarkers for endogenous MDD

| Gene Symbol | Gene name (number of transcripts) | Gene Symbol | Gene name (number of transcripts) |
|---|---|---|---|
| FAM46A | family with sequence similarity 46, member A (7) | NRP1 | neuropilin 1 (18) |
| MARCKS | myristoylated alanine-rich protein kinase C substrate(1) | PDE6D | phosphodiesterase 6D, cGMP-specific, rod, delta (6) |
| ATP2C1 | ATPase Ca++ transporting, type 2C, member 1 (6) | PPP1R3B | protein phosphatase 1, regulatory subunit 3B (1) |
| NAGA | N-acetyl-galactosaminidase, alpha (5) | PRPF18 | PRP18 pre-mRNA processing factor 18 homolog (5) |
| TLR7 | toll-like receptor 7 (2) | RNASEL | ribonuclease L (2) |
| ADCY3 | adenylate cyclase 3 (15) | SEMA4A | semaphorin 4A (16) |

TABLE 1-continued

Biomarkers for endogenous MDD

| Gene Symbol | Gene name (number of transcripts) | Gene Symbol | Gene name (number of transcripts) |
|---|---|---|---|
| ANXA4 | annexin A4 (13) | SERPINB1 | serpin peptidase inhibitor, clade B, member 1 (5) |
| APP | amyloid beta(A4) precursor protein (20) | SLFN12 | schlafen family member 12 (8) |
| ASAH1 | N-acylsphingosine amidohydrolase 1 (4) | SMPDL3A | sphingomyelin phosphodiesterase, acid-like 3A (2) |
| ATP6AP2 | ATPase, H+ transporting, lysosomal accessory protein 2 (7) | SNX10 | sorting nexin 10 (8) |
| BCAT1 | branched chain aminotransferase 1, cytosolic (2) | SOAT1 | sterol O-acyltransferase 1 (2) |
| CAST | calpastatin (13) | SYNJ1 | synaptojanin 1 (19) |
| CD59 | CD59 molecule, complement regulatory protein (7) | TCF7L2 | transcription factor 7-like 2 (16) |
| CEBPA | CCAAT/enhancer binding protein, alpha (1) | ZNF291/ SCAPER | S-phase cyclin A-associated protein (2) |
| CITED2 | Cbp/p300-interacting transactivator, with Glu/Asp-rich carboxy-terminal domain, 2 (2) | FUCA2 | fucosidase, alpha-L-2, plasma (6) |
| FOS | FBJ murine osteosarcoma viral oncogene homolog (1) | ATP11C | ATPase, class VI, type 11C (11) |
| IDH1 | isocitrate dehydrogenase 1 (NADP+), soluble (13) | MAF | v-maf oncogene homolog (2) |
| IGSF4A/ CADM1 | cell adhesion molecule 1 (3) | GNAQ | guanine nucleotide binding protein alpha stimulating activity polypeptide 1 (2) |
| IL13RA1 | interleukin 13 receptor, alpha 1 (4) | MAST4 | microtubule associated serine/threonine kinase family member 4 (30) |
| KLF4 | Kruppel-like factor 4 (8) | FMR1 | fragile X mental retardation 1 (13) |
| LRRC40 | leucine rich repeat containing 40 (1) | PTPRM | protein tyrosine phosphatase, receptor type, mu polypeptide (4) |

Example 2

Biomarkers of Chronic Stress States

During development of embodiments of the present invention, chronic-stress experiments were conducted utilizing four phylogenetically, physiologically and behaviorally different strains of rats to identify chronic stress-related peripheral biomarkers. Genetic polymorphisms between the strains ranged from 25.9% to 66%, representing a substantial inter-strain variation that is aimed to mimic individual variation among the human subjects. Blood transcripts with the largest fold changes in response to chronic stress across all four strains were identified as chronic stress markers.

For the isolation of the chronic stress markers, whole blood were collected into PAXgene Blood RNA tubes from non-stressed and chronically stressed Fisher-344 (F344), Brown Norway (BN-SS), Lewis (Lew), and Wistar Kyoto (WKY) male rats. Blood microarray analyses were carried out using the Illumina Sentrix® Rat (Ref-12) Expression BeadChip, version 1.0, release 1. Transcripts were selected with significant, differences between chronic stress and control and with an absolute fold change of greater than 1.2. 117 genes in the blood were identified that were differentially expressed between the CRS and no stress (NS) conditions and had human orthologues (See Table 2).

TABLE 2

| Gene symbol | Gene name |
|---|---|
| ADD2 | adducin 2 |
| ADIPOR1 | adiponectin receptor 1 |
| ARF5 | ADP-ribosylation factor 5 |
| AHSP | alpha hemoglobin stabilizing protein (ERAF) |
| ANK1 | ankyrin 1, erythroid |
| APOL3 | apolipoprotein L, 3 |
| ARIH1 | ariadne ubiquitin-conjugating enzyme E2 binding protein homolog 1 |

TABLE 2-continued

| Gene symbol | Gene name |
|---|---|
| AMFR | autocrine motility factor receptor |
| BOLA3 | bolA homolog 3 |
| CHP | calcium binding protein p22 |
| CA2 | carbonic anhydrase 2 |
| CA1 | carbonic anhydrase 1 |
| CSNK1G2 | casein kinase 1, gamma 2 |
| CAT | catalase |
| CTSB | cathepsin B |
| CD3D | CD3 antigen delta polypeptide |
| CD37 | CD37 antigen |
| CD82 | CD82 antigen |
| CREG1 | cellular repressor of E1A-stimulated genes |
| CDR2 | cerebellar dergeneration-related 2 |
| C7orf70 | chromosome 7 open reading frame 70 |
| C2 | complement component 2 |
| CXXC1 | CXXC finger 1 |
| CMAS | cytidine monophospho-N-acetylneuraminic acid synthetase |
| DDX24 | DEAD box polypeptide 24 |
| DENND5A | DENN/MADD domain containing 5A |
| DGKA | diacylglycerol kinase, alpha |
| DNAJB6 | DnaJ homolog, subfamily B, member 6 |
| DYRK3 | dual-specificity tyrosine--phosphorylation regulated kinase 3 |
| DYNC1H1 | dynein, cytoplasmic, heavy chain 1 |
| DYNLL1 | dynein, cytoplasmic, light chain 1 |
| EMB | embigin |
| EPB42 | erythrocyte membrane protein band 4.2 |
| FBXO7 | F-box only protein 7 |
| FAM117A | family with sequence similarity 117, member A |

TABLE 2-continued

| Gene symbol | Gene name |
|---|---|
| FAM125A | family with sequence similarity 125, member A |
| FECH | ferrochelatase |
| FLNA | Filamin A |
| FMNL1 | formin-like 1 |
| FN3K | fructosamine-3-kinase |
| FUS | fusion in malignant liposarcoma) |
| FYN | fyn proto-oncogene |
| GATA1 | GATA binding protein 1 |
| GCLM | glutamate cysteine ligase, modifier subunit |
| ERICH1 | glutamate-rich 1 |
| GLRX5 | glutaredoxin 5 |
| GPX4 | glutathione peroxidase 4 |
| GLTP | Glycolipid transfer protein |
| GLG1 | golgi apparatus protein 1 |
| GGA3 | golgi associated, gamma adaptin ear containing, ARF binding protein 3 |
| GCH1 | GTP cyclohydrolase 1 |
| HPS1 | Hermansky-Pudlak syndrome 1 homolog |
| SUV420H2 | histone-lysine N-methyltransferase |
| HAGH | hydroxyacyl glutathione hydrolase |
| INSL3 | insulin-like 3 |
| IRF3 | interferon regulatory factor 3 |
| IFRD2 | interferon-related developmental regulator 2 |
| ISG12 | interferon, alpha-inducible protein 27-like |
| ISCU | iron-sulfur cluster scaffold homolog |
| KIAA1539 | KIAA1539 |
| LEPROTL1 | leptin receptor overlap transcript-like 1 |
| LAPTM5 | lysosomal-associated protein transmembrane 5 |
| MTVR2 | mammary tumor virus receptor 2 |
| MXD1 | max dimerization protein 1 |
| MEMO1 | mediator of cell motility 1 |
| MIIP | migration and invasion inhibitory protein |
| MAP2K3 | mitogen activated protein kinase kinase 3 |
| NAT9 | N-acetyltransferase 9 |
| NBEAL2-PS1 | neurobeachin-like 2, pseudogene 1 |
| NXT1 | NTF2-related export protein 1 |
| NOP56 | nucleolar protein 56 |
| PCYT2 | phosphate cytidylyltransferase 2, ethanolamine |
| PLCG2 | phospholipase C, gamma 2 |
| PARP10 | poly (ADP-ribose) polymerase family, member 10 |
| KTCD20 | potassium channel tetramerisation domain containing 20 |
| PAQR9 | progestin and adipoQ receptor family member IX |
| PSME1 | protease 28 subunit, alpha |
| PSMB10 | proteasome subunit, beta type 10 |
| PSMB3 | proteasome subunit, beta type 3 |
| PSMB8 | proteasome subunit, beta type 8 |
| PPP1R10 | protein phosphatase 1, subunit 10 |
| PTP4A3 | protein tyrosine phosphatase 4a3 |
| RAB10 | member RAS oncogene family |
| RTP4 | receptor (chemosensory) transporter protein 4 |
| MAF1 | Repressor of RNA polymerase III transcription MAF1 homolog |
| SELO | selenoprotein O |
| 1-Sep | septin 1 |
| SERBP1 | SERPINE1 mRNA binding protein 1 |
| SHARPIN | shank-interacting protein |

TABLE 2-continued

| Gene symbol | Gene name |
|---|---|
| SMAP2 | small ArfGAP2 |
| SLC16A10 | solute carrier family 16, member 10 |
| SLC4A1 | solute carrier family 4, member 1 |
| SPTAN1 | spectrin, alpha, non-erythrocytic 1 |
| SYK | spleen tyrosine kinase |
| ST3GAL2 | ST3 beta-galactoside alpha-2,3-sialyltransferase 2 |
| STRADB | STE20-related kinase adaptor beta |
| STRA8 | stimulated by retinoic acid gene 8 |
| TSPAN8 | tetraspanin 8 |
| TREX1 | 3-5 exonuclease TREX1 |
| ATP5G1 | ATP synthase, H+ transporting, mitochondrial F0 complex, subunit c, isoform 1 |
| TMCC2 | transmembrane and coiled-coil domain family 2 |
| TMEM183A | transmembrane protein 183A |
| TRIM10 | tripartite motif-containing 10 |
| TMOD1 | tropomodulin 1 |
| TINAGL1 | tubulointerstitial nephritis antigen-like 1 |
| TIE1 | tyrosine kinase receptor 1 |
| UBAC1 | ubiquitin associated domain containing 1 |
| USP8 | ubiquitin specific protease 8 |
| UBE2C | ubiquitin-conjugating enzyme E2C |
| UBE2O | ubiquitin-conjugating enzyme E2O |
| UBE2R2 | ubiquitin-conjugating enzyme E2R 2 |
| UROD | uroporphyrinogen decarboxylase |
| VAMP3 | vesicle-associated membrane protein 3 |
| VKORC1L1 | vitamin K epoxide reductase complex, subunit 1-like 1 |
| WDR26 | WD repeat domain 26 |
| WDR45 | WD repeat domain 45 |
| ZAP70 | zeta-chain associated protein kinase 70 kDa |

Example 3

Identification of Adolescent MDD Biomarkers

Experiments were conducted during the development of embodiments of the invention to identify biomarkers for MDD in adolescent human subjects.

Males and females, 15-18 years of age, were recruited through other research studies at the Research Institute at Nationwide Children's Hospital (RINCH), the Nationwide Children's Hospital (NCH) Adolescent Medicine Clinic, NCH Behavioral Medicine Clinic, and community flyers (Table 3). Subjects were recruited into either an MDD or No Disorder (ND) group, based on results from a youth and a parent full, standardized, structured psychiatric interview. Exclusion criterion for the MDD group included: younger or older than 15-18 years; major medical illness; antidepressant use; bipolar disorder; psychosis; pregnancy; mental retardation. Additional exclusion criterion for the No Disorder (ND) group was any lifetime psychiatric disorder.

TABLE 3

Adolescent Project Sample Characteristics

| Diagnosis | N | Gender | Age Mean | Age Range | Race White | Race Black |
|---|---|---|---|---|---|---|
| MDD | 1 | M | 15 | 15 | | X |
| | 3 | F | 17 | 17 | X (3) | |
| ND | 2 | M | 16.5 | 15-18 | X | X |
| | 3 | F | 15.5 | 15-16 | X (2) | X |

Consent/assent or youth consent (18 year-olds) were obtained. 15 cc of blood was drawn into 2 PaxGene tubes at 4 PM from each youth. Youth and parent were then interviewed separately about the youth's medical and psychiatric history. Psychiatric diagnoses were made with the Computerized Diagnostic Interview Schedule for Children (C-DISC)-Youth and Parent Versions, a valid and reliable interview that we have used in over 300 youths; it assesses every Axis I disorder and takes 2-3 hours to administer. Diagnoses of MDD were counted from either parent or youth report, although in all but one subject, symptoms of depression were reported by both informants.

Blood samples with only numbers as identification, collected in PAXgene tubes, were processed for RNA using the PAXgene Blood RNA Kit (Qiagen Inc.). RNA yields from 2.5 ml human whole blood were >14 μg with an average 260/280 ratio of >1.7. cDNA was prepared using random primers and the TaqMan RT reagents (ABI). RNA quantification was performed using SYBR Green based real time PCR technology with the ABI Prism 7300 (Applied Biosystems, Foster City, Calif.). 18s rRNA was used as an internal control. Specific primers were designed to amplify the human homolog of the rat microarray probe region using the PRIMER EXPRESS Software (version 3.0, PE Applied Biosystems). Melting curve analyses and no template control reactions were performed to confirm appropriate target amplification.

Statistically significant differences were found between the two groups on 3 of the comparisons (SEE FIG. 1) and 13 of the effect sizes were in the large range (Table 4). These data indicate that a larger sample would yield statistically significant differences in more of the biomarkers (e.g. the majority).

TABLE 4

Quantitative RT-PCR pilot results from blood RNA: adolescent candidate biomarkers for MDD.

| Gene | Control (mean +/− SD) | Depressed (mean +/− SD) | Effect size (Cohen's d) |
|---|---|---|---|
| ADCY3 | 0.822 +/− 0.230 | 0.653 +/− 0.127 | 0.909## |
| ATP2C1 | 0.634 +/− 0.404 | 0.842 +/− 0.186 | −0.660## |
| CD59 | 0.879 +/− 0.196 | 0.779 +/− 0.061 | 0.680## |
| EDG2 | 0.853 +/− 0.250 | 0.842 +/− 0.429 | 0.030 |
| FAM46A | 1.212 +/− 0.278 | 0.970 +/− 0.103 | 1.152## |
| FGFR1 | 1.348 +/− 0.755 | 1.085 +/− 0.229 | 0.470 |
| FMR1 | 1.350 +/− 0.020 | 1.090 +/− 0.189 | 1.320## |
| FOS | 0.799 +/− 0.399 | 1.001 +/− 0.698 | −0.392 |
| GNAQ | 1.075 +/− 0.258 | 1.272 +/− 0.249 | −0.776## |
| IGSF4A* | 4.849 +/− 1.566 | 2.121 +/− 0.944 | 2.109## |
| MAP* | 1.626 +/− 0.438 | 0.948 +/− 0.247 | 1.901## |
| MARCKS | 0.853 +/− 0.476 | 1.212 +/− 0.262 | −0.935## |
| NAGA | 0.839 +/− 0.321 | 0.558 +/− 0.090 | 1.189## |
| PDE6D | 0.878 +/− 0.221 | 0.803 +/− 0.129 | 0.413 |
| PTPRM | 1.271 +/− 0.158 | 0.966 +/− 0.401 | 0.716## |
| SLC6A4 | 0.866 +/− 0.381 | 0.982 +/− 0.407 | −0.294 |
| TLR7 | 0.775 +/− 0.303 | 0.148 +/− 0.740 | 1.054## |
| ZNF291* | 1.080 +/− 0.228 | 0.780 +/− 0.129 | 1.617## |

*$p < 0.05$; ##Large effect sizes

Experiments were conducted in which blood samples were analyzed in participants with MDD or No Disorder using the same diagnostic criteria as above. In this set of adolescents, Chronic Stressor Exposure was also assessed using the Childhood Trauma Questionnaire (CTQ). Correlations between the chronic stress model genes, 15 genes selected from Table 2 (highlighted in gray in Table 2) with an absolute fold change between 1.28-1.95, and the stressor/stress scale scores of chronic stress, the CTQ Total Score, (See Table 5).

TABLE 5

Spearman correlation between blood transcript abundance of some chronic stress blood markers and stressor/stress scale scores

| | | CDR2 | CMAS | KIAA1539 | PSME1 | PTP4A3 | FECH | IRF3 |
|---|---|---|---|---|---|---|---|---|
| CTQ Total Score | rho | .473 | .525 | .513 | .605 | .531 | .439 | .499 |
| | P (2-tailed) | .064 | .037 | .042 | .013 | .034 | .089 | .049 |
| | N | 16 | 16 | 16 | 16 | 16 | 16 | 16 |
| Emotional Abuse | rho | .271 | .230 | .463 | .555 | .433 | .253 | .466 |
| | P (2-tailed) | .310 | .391 | .071 | .026 | .094 | .345 | .069 |
| | N | 16 | 16 | 16 | 16 | 16 | 16 | 16 |
| Physical Abuse | rho | −.026 | .168 | .145 | .129 | −.050 | .016 | −.010 |
| | P (2-tailed) | .924 | .535 | .592 | .635 | .853 | .952 | .971 |
| | N | 16 | 16 | 16 | 16 | 16 | 16 | 16 |
| Sexual Abuse | rho | .203 | .162 | .216 | .045 | .076 | .173 | .039 |
| | P (2-tailed) | .451 | .549 | .422 | .867 | .781 | .522 | .886 |
| | N | 16 | 16 | 16 | 16 | 16 | 16 | 16 |
| Emotional Neglect | rho | .498 | .571 | .461 | .585- | .496 | .468 | .538 |
| | P (2-tailed) | .050 | .021 | .073 | .017 | .051 | .067 | .032 |
| | N | 16 | 16 | 16 | 16 | 16 | 16 | 16 |
| Physical Neglect | rho | .494 | .521- | .392 | .480 | .383 | .460 | .472 |
| | P (2-tailed) | .052 | .038 | .133 | .060 | .143 | .073 | .065 |
| | N | 16 | 16 | 16 | 16 | 16 | 16 | 16 |

Effect sizes were calculated between subjects with No disorder and MDD (See Table 6).

TABLE 6

Effect sizes for the MDD vs. No Disorder comparison for both sets of blood biomarkers

| | | Mean DCT[a] | SD | Fold Change[b] | Effect Size |
|---|---|---|---|---|---|
| "Endogenous Depression" marker | | | | | |
| ATP11C | No Disorder | 14.9232 | .74081 | 1 | −0.8361 |
| | MDD | 15.1088 | .45897 | 0.87928 | |
| CD59 | No Disorder | 13.9868 | .59346 | 1 | −0.7811 |
| | MDD | 14.3945 | .43889 | 0.75382 | |
| FAM46A | No Disorder | 15.6206 | .62560 | 1 | −0.0036 |
| | MDD | 15.6184 | .60388 | 1.00153 | |
| IGSF4A | No Disorder | 16.5055 | 2.63519 | 1 | −0.5909 |
| | MDD | 17.7116 | 1.17864 | 0.43344 | |
| MAF | No Disorder | 17.7071 | .88667 | 1 | −0.6169 |
| | MDD | 18.1609 | .54407 | 0.73012 | |
| MARKS | No Disorder | 13.2903 | 1.42679 | 1 | −0.3974 |
| | MDD | 13.7691 | .93121 | 0.71757 | |
| NAGA | No Disorder | 13.9092 | .83357 | 1 | −0.2849 |
| | MDD | 14.1327 | .73240 | 0.85649 | |
| RAPH1 | No Disorder | 15.7073 | 2.56428 | 1 | −0.6208 |
| | MDD | 16.9376 | 1.02885 | 0.42623 | |
| TLR7 | No Disorder | 15.4338 | .85478 | 1 | −0.0035 |
| | MDD | 15.4311 | .66038 | 1.00187 | |
| UBE3A | No Disorder | 15.1981 | 1.65462 | 1 | −0.2701 |
| | MDD | 15.5834 | 1.12891 | 0.76562 | |
| ZNF291 | No Disorder | 16.1619 | 1.15379 | 1 | −0.3600 |
| | MDD | 16.4937 | .60660 | 0.79454 | |
| "Chronic Stress" marker | | | | | |
| AHSP | No Disorder | 12.9605 | .89321 | 1 | −0.4637 |
| | MDD | 12.5939 | .67266 | 1.28931 | |
| AMFR | No Disorder | 13.5744 | 1.68521 | 1 | −0.5673 |
| | MDD | 14.2731 | .44021 | 0.61613 | |
| CAT | No Disorder | 14.6880 | 1.08626 | 1 | −0.5376 |
| | MDD | 15.1444 | .47227 | 0.72880 | |
| CDR2 | No Disorder | 14.8752 | .65338 | 1 | −0.8657 |
| | MDD | 15.3368 | .36033 | 0.72618 | |
| CMAS | No Disorder | 15.5308 | 2.43662 | 1 | −0.766 |
| | MDD | 16.9309 | .72694 | 0.37890 | |
| DGKA | No Disorder | 11.2385 | 1.41685 | 1 | −0.0716 |
| | MDD | 11.1497 | 1.03203 | 1.06349 | |
| EMB | No Disorder | 12.7808 | 1.05224 | 1 | −0.1918 |
| | MDD | 12.9464 | .59428 | 0.89156 | |
| FECH | No Disorder | 13.4058 | 1.15795 | 1 | −0.4100 |
| | MDD | 13.7887 | .63539 | 0.76689 | |
| GCLM1 | No Disorder | 16.2397 | .91531 | 1 | −0.1939 |
| | MDD | 16.3997 | .71448 | 0.89503 | |
| GGA3 | No Disorder | 15.3662 | .88044 | 1 | −0.2513 |
| | MDD | 15.5736 | .78498 | 0.86610 | |
| IRF3 | No Disorder | 13.0719 | .95953 | 1 | −0.3423 |
| | MDD | 13.3472 | .61042 | 0.82628 | |
| KIAA1539 | No Disorder | 13.4514 | 1.32581 | 1 | −0.0142 |
| | MDD | 13.4686 | 1.07637 | 0.98815 | |
| PSME1 | No Disorder | 11.1975 | .53582 | 1 | −0.5231 |
| | MDD | 11.4749 | .52421 | 0.82508 | |
| PTP4A3 | No Disorder | 14.9475 | .94725 | 1 | −0.7703 |
| | MDD | 15.5894 | .68885 | 0.64087 | |
| SLC4A1 | No Disorder | 13.1906 | 1.29940 | 1 | −0.0676 |
| | MDD | 13.2694 | 1.01411 | 0.94684 | |

[a]DCT = CTtarget gene-CThousekeeping gene; [Target]/[Housekeeping] = $2^{-DCT}$;
[b]Fold Change = $2^{-DCT(MDD)-DCT(ND)}$ Additional analyses also shown that some of the potential blood markers can distinguish patients with MDD only from patients with MDD and Anxiety. Effects sizes for this comparison are shown in Table 7.

TABLE 7

Comparison between MDD only and MDD with Anxiety

| | Diagnoses, Youth or Parent | Mean | SD | Effect Size |
|---|---|---|---|---|
| Endogenous Depression markers | | | | |
| ATP11C | MDD Only | 15.2596 | .23454 | 0.49 |
| | MDD + Anxiety Disorder | 15.0147 | .55075 | |
| CD59 | MDD Only | 14.6551 | .09019 | 0.94 |
| | MDD + Anxiety Disorder | 14.2498 | .49290 | |
| FAM46A | MDD Only | 15.3099 | .51630 | −0.78 |
| | MDD + Anxiety Disorder | 15.7898 | .60560 | |
| IGSF4A | MDD Only | 18.4211 | .68470 | 0.95 |
| | MDD + Anxiety Disorder | 17.3174 | 1.23838 | |
| MAF | MDD Only | 18.1239 | .58738 | −0.10 |
| | MDD + Anxiety Disorder | 18.1815 | .55424 | |
| MARKS | MDD Only | 13.5260 | .57322 | −0.37 |
| | MDD + Anxiety Disorder | 13.9042 | 1.08966 | |
| NAGA | MDD Only | 13.6951 | .53240 | −0.94 |
| | MDD + Anxiety Disorder | 14.3758 | .73741 | |
| RAPH1 | MDD Only | 17.1122 | .82167 | 0.25 |
| | MDD + Anxiety Disorder | 16.8285 | 1.18044 | |
| TLR7 | MDD Only | 15.0418 | .56444 | −0.93 |
| | MDD + Anxiety Disorder | 15.6474 | .63404 | |
| UBE3A | MDD Only | 15.8918 | .32713 | 0.41 |
| | MDD + Anxiety Disorder | 15.3906 | 1.41887 | |
| ZNF291 | MDD Only | 16.1685 | .59014 | −0.82 |
| | MDD + Anxiety Disorder | 16.6744 | .56655 | |
| Chronic Stress markers | | | | |
| AHSP | MDD Only | 12.3232 | .52023 | −0.59 |
| | MDD + Anxiety Disorder | 12.7443 | .72712 | |
| AMFR | MDD Only | 13.9849 | .35561 | −1.06 |
| | MDD + Anxiety Disorder | 14.4332 | .41345 | |
| CAT | MDD Only | 14.9740 | .60841 | −0.55 |
| | MDD + Anxiety Disorder | 15.2509 | .37033 | |
| CDR2 | MDD Only | 15.5524 | .20734 | 0.99 |
| | MDD + Anxiety Disorder | 15.2020 | .37955 | |
| CMAS | MDD Only | 17.3159 | .28832 | 0.85 |
| | MDD + Anxiety Disorder | 16.6903 | .82848 | |
| DGKA | MDD Only | 10.3071 | .68101 | −1.47 |
| | MDD + Anxiety Disorder | 11.6179 | .89919 | |
| EMB | MDD Only | 13.0919 | .25565 | 0.36 |
| | MDD + Anxiety Disorder | 12.8555 | .73724 | |
| FECH | MDD Only | 13.7521 | .83616 | −0.08 |
| | MDD + Anxiety Disorder | 13.8091 | .55241 | |
| GCLM1 | MDD Only | 16.7181 | .24730 | 0.69 |
| | MDD + Anxiety Disorder | 16.2007 | .85000 | |
| GGA3 | MDD Only | 15.2748 | .63735 | −0.58 |
| | MDD + Anxiety Disorder | 15.7604 | .84886 | |
| IRF3 | MDD Only | 13.0075 | .60782 | −0.86 |
| | MDD + Anxiety Disorder | 13.5359 | .55548 | |
| KIAA1539 | MDD Only | 12.8294 | .88024 | −0.99 |
| | MDD + Anxiety Disorder | 13.8681 | 1.03397 | |
| PSME1 | MDD Only | 11.6564 | .40741 | 0.52 |
| | MDD + Anxiety Disorder | 11.3615 | .58138 | |
| PTP4A3 | MDD Only | 15.7955 | .62373 | 0.45 |
| | MDD + Anxiety Disorder | 15.4607 | .73612 | |
| SLC4A1 | MDD Only | 12.6948 | 1.26028 | −0.88 |
| | MDD + Anxiety Disorder | 13.5886 | .74571 | |

Example 4

Identification of Adult MDD Biomarkers

Experiments were conducted during the development of embodiments of the invention to identify biomarkers for MDD in adult human subjects. Demographic data and depression scores using the PHQ-9 were obtained for adult subjects (Table 8).

TABLE 8

|         | No. | Gender | Age Mean | Age Range | PHQ-9 Mean | PHQ-9 Range |
|---------|-----|--------|----------|-----------|------------|-------------|
| Patient | 2   | M      | 48       | 40-56     | 20.5       | 14-27       |
|         | 4   | F      | 40       | 25-56     | 11         | 12-22       |
| Control | 2   | M      | 50.5     | 33-68     | 2          | 0-4         |
|         | 4   | F      | 39       | 24-57     | 1.5        | 0-5         |

Figure 2:
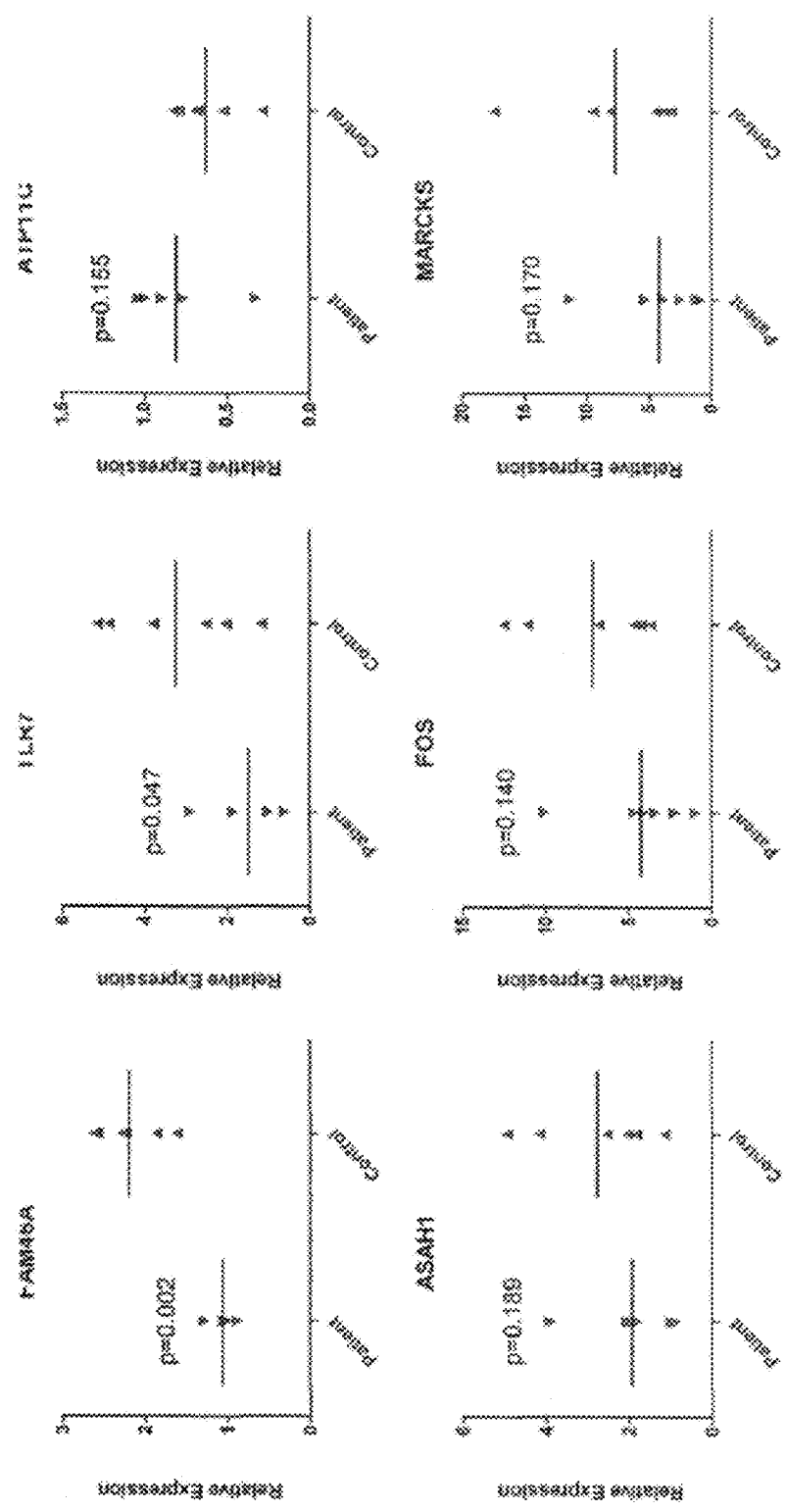
FIG. 2 shows plots validating adult biomarker genes by quantitative RT-PCR; RNA was prepared from the blood of adult subjects with MDD, and age- and race-matched controls; the amounts of specific mRNA were normalized to 18s rRNA expression.

Blood samples were collected in PAXGENE tubes, and processed for RNA using the PAXGENE blood RNA Kit (QIAGEN). RNA yields from 2.5 ml human whole blood were >14 µg with an average 260/280 ratio of >1.7. cDNA was prepared using random primers and the TaqMan RT reagents (ABI). RNA quantification was performed using SYBR Green based real time PCR technology with the ABI Prism 7300 (Applied Biosystems, Foster City, Calif.). 18s rRNA was used as internal control. There were significant differences in the expression of FAM46A and TLR7 between patients with MDD and controls (SEE FIG. 2). FAM46A (Family with sequence similarity 46, member A) is a gene with unknown function that encodes a 437-amino acid protein with a calculated molecular mass of 49.2 kD. Database analysis indicates that FAM46A is conserved from yeast to human.

Experiments were conducted employing subjects with the characteristics described in Table 9.

TABLE 9

|          | No. | Gender | Age, Mean | Age Range | HAM-score before treatment (mean +/− SD) | HAM-score after treatment (mean +/− SD) |
|----------|-----|--------|-----------|-----------|------------------------------------------|------------------------------------------|
| MDD      | 24  | F      | 48.7      | 23-83     | 23.3 +/− 3.6                             | 12.4 +/− 7.7                             |
|          | 10  | M      | 50.3      | 34-79     | 22.5 +/− 4.4                             | 14.8 +/− 3.5                             |
| Controls | 24  | F      | 48.4      | 23-84     | 4.2 +/− 2.4                              | ND                                       |
|          | 10  | M      | 53.6      | 34-79     | 4.1 +/− 2.0                              | ND                                       |

Race: Females, 16.6% African American and 8% Hispanic. Males all Caucasian

Abundance of the following transcripts was significantly different between subjects with MDD before cognitive behavioral therapy and their matched controls: ADCY3 ($p=0.0028$), ASAH1 (0.0263), FAM46A ($p=0.0039$), IGSF4A/CADM1 (0.001), MARCKS ($p=0.0008$), NAGA ($p=0.0312$), TLR7 ($p=0.0019$). HAM scores correlated significantly (Spearman correlation) with transcript levels of ATP11C ($p=0.0089$) and FAM46A ($p=0.0045$). Additional significant results were obtained for CD59, CDR2, CMAS, PSME1 and DGKA.

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A composition comprising between 4 and 40 cDNAs, wherein at least four of the cDNAs are selected from the list consisting of RAPH1, AMFR, ZNF291, PTP4A3, ATP11C, and, MAF.

2. The composition of claim 1, wherein the panel comprises RAPH1, AMFR, ZNF291, PTP4A3, ATP11C, and, MAF cDNAs.

* * * * *